(12) United States Patent
Hill et al.

(10) Patent No.: US 6,616,934 B1
(45) Date of Patent: Sep. 9, 2003

(54) CLEAR SILICONE MICROEMULSIONS

(75) Inventors: Randal Myron Hill, Midland, MI (US); Zuchen Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/575,258

(22) Filed: May 22, 2000

(51) Int. Cl.⁷ .......................... A61K 31/74; A61K 6/00; A61K 7/00; A01N 25/00
(52) U.S. Cl. ................. 424/401; 424/78.03; 514/937
(58) Field of Search .............. 424/78.03, 401; 524/837; 514/937

(56) References Cited

U.S. PATENT DOCUMENTS

| | | | | |
|---|---|---|---|---|
| 5,364,633 A | | 11/1994 | Hill | 424/450 |
| 5,486,566 A | * | 1/1996 | Katsoulis | 524/773 |
| 5,623,017 A | | 4/1997 | Hill | 524/860 |
| 5,705,562 A | | 1/1998 | Hill | 524/731 |
| 5,707,613 A | * | 1/1998 | Hill | 424/78.03 |
| 5,879,671 A | | 3/1999 | Halloran | 424/70 |
| 5,948,855 A | * | 9/1999 | Lin et al. | 524/837 |
| 6,017,546 A | * | 1/2000 | Glover | 424/401 |
| 6,133,370 A | * | 10/2000 | Gutek et al. | 524/588 |

* cited by examiner

Primary Examiner—Sreeni Padmanabhan
Assistant Examiner—Lauren Q. Wells
(74) Attorney, Agent, or Firm—Jim L. De Cesare

(57) ABSTRACT

Spontaneously formed highly stable clear water-in-oil microemulsions containing only small amounts of water can be prepared by combining and simply hand shaking (i) 0.1 to 9 percent by weight of water; (ii) greater than 80 percent by weight of a volatile cyclic alkyl siloxane or volatile linear alkyl siloxane; and (iii) 3 to 10 percent by weight of certain silicone polyether surfactants. The microemulsions are useful in personal care applications.

6 Claims, No Drawings

CLEAR SILICONE MICROEMULSIONS

CROSS-REFERENCE TO RELATED APPLICATIONS

Not applicable.

STATEMENT REGARDING FEDERALLY SPONSORED-RESEARCH OR DEVELOPMENT

Not applicable.

REFERENCE TO A MICROFICHE APPENDIX

Not applicable.

FIELD OF THE INVENTION

This invention relates to improvements in spontaneously formed clear microemulsions generally described in U.S. Pat. No. 5,705,562 (Jan. 6, 1998), which is assigned to the same assignee as this invention.

BACKGROUND OF THE INVENTION

The focus of U.S. Pat. No. 5,705,562 is on (i) oil-in-water (O/W) microemulsions, and (ii) silicone polyether surfactants which are water soluble; whereas the focus of the present invention is on (i) water-in-oil (W/O) microemulsions, and (ii) silicone polyether surfactants which are oil soluble, with the intention of preparing distinctly W/O microemulsions containing only relatively small amounts of water.

In particular, a side-by-side comparison between this invention and U.S. Pat. No. 5,705,562 is shown in Table 1. In Table 1, the parameters a–c, m, n, and x–z, represent integers in the structure of silicone polyether surfactants shown more fully hereinafter.

TABLE 1

| Parameter | U.S. Pat. No. 5,705,562 | The Present Invention |
|---|---|---|
| Amount of Water | 20–60 Percent | 0.1–9 Percent |
| Amount of Oil | 40–80 Percent | 81–96.9 Percent |
| Amount of Surfactant | 5–70 Percent | 3–10 Percent |
| a | 3–6 | 0–6 |
| b | 4–20 | 2–6 |
| c | 0–5 | 0–3 |
| x | 0–3 | 0–3 |
| y | 1–3 | 1–3 |
| z | 0–2 | 0–2 |
| m | 3–5 | 3–5 |
| n | 1 | 1 |

What has been unexpectedly discovered herein is that when b is limited to the range of 2 to 6, rather than 4 to 20 as in U.S. Pat. No. 5,705,562, the silicone polyether surfactants are only oil soluble and form distinctly water-in-oil microemulsions containing only 0.1 to 9 percent by weight of water. This is a greater than two-fold reduction, compared to the microemulsions containing 20 to 60 percent by weight of water in U.S. Pat. No. 5,705,562.

In addition, it is possible to prepare distinctly water-in-oil microemulsions containing greater than 80 percent by weight of an oil component, compared to microemulsions in U.S. Pat. No. 5,705,562 which contain 40 to 80 percent by weight oil. A third distinction according to this invention is that much less silicone polyether surfactant is needed, i.e., 3 to 10 percent by weight, compared to 5–70 percent by weight in U.S. Pat. No. 5,705,562.

BRIEF SUMMARY OF THE INVENTION

The invention is directed to a microemulsion containing (i) 0.1 to 9 percent by weight of water; (ii) greater than 80 percent by weight of a cyclic alkyl siloxane of the formula $(R_2SiO)p$ or a linear alkyl siloxane of the formula $R_3SiO(R_2SiO)_qSiR_3$ in which R is an alkyl group containing 1–6 carbon atoms, p is 3–6, and q is 0–5; and (iii) 3 to 10 percent by weight of silicone polyether having an average structure represented by one of the following:

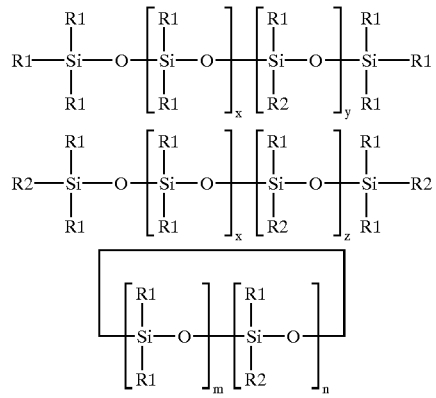

where R1 is an alkyl group containing 1–6 carbon atoms; R2 represents the radical $-(CH_2)_aO(_aO(C_2H_4O)_b(C_3H_6O)_cR_3$; x has a value of 0–3; y has a value of 1–3; z has a value of 0–2; m has a value of 3–5; n is one; a has a value of 0–6; b has a value of 2–6; c has a value of 0–3; and R3 is hydrogen, a methyl radical, or an acyl radical.

Preferably, the alkyl siloxane is a cyclic methyl siloxane of the formula $\{(CH_3)_2SiO\}_p$ or linear methyl siloxane of the formula $(CH_3)_3SiO\{(CH_3)_2SiO\}_qSi(CH_3)_3$ in which p is 3–6 and q is 0–5, respectively.

By greater than 80 percent by weight is meant that the microemulsion should contain 81 to 96.9 percent by weight of the alkyl siloxane. Most preferred, are microemulsions containing greater than 85 percent by weight of alkyl siloxane.

The invention is also directed to personal care products containing these microemulsions, and to methods of treating hair or skin by applying to hair or skin compositions containing these microemulsions.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

According to this invention, optically clear silicone microemulsions can be formed with very little input of mechanical energy for mixing the components. Thus, a ternary composition of water, a volatile cyclic or linear alkyl siloxane, and a short-chain or low molecular weight silicone polyether, spontaneously provides optically clear microemulsions when combined with only hand agitation.

As used herein, the term emulsion or macroemulsion means a dispersion of one immiscible liquid in another, in the form of droplets, with diameters approximately in the range of 100–1,000 nanometer (0.1–1.0 micron/1,000–10, 000 angstrom Å). In contrast, a microemulsion means a transparent, thermodynamically stable, dispersion of two or more immiscible liquids and a surfactant. More particularly, microemulsions are generally considered to be spontaneously self-assembling one phase compositions.

Microemulsions are clear or transparent because they contain domains of water or oil smaller than the wavelength of visible light, generally considered to be on order of magnitude of about 10–100 nanometer. For example, microemulsions may contain oil domains in a water continuous matrix (O/W), water domains dispersed in oil (W/O), or they may form a bicontinuous structure. They are characterized by an ultra-low interfacial tension between oil and water domains.

A microemulsion can be recognized by some inherent characteristics which are (i) it contains oil, water, and surfactant; (ii) there is generally a high concentration of surfactant relative to oil; (iii) the system is optically clear; (iv) the system cannot be separated by centrifugation; and (v) the system forms spontaneously.

For purposes of this invention, therefore, an emulsion is considered as containing particles or droplets having an average diameter of more than 100 nanometer (0.1 micron/1,000 angstrom Å), whereas a microemulsion contains domains of oil or water having an average diameter of less than 100 nanometer (0.1 micron/1,000 angstrom Å).

Generally, clarity or transparency is controlled to a great extent by the size of the dispersed phase. The scattering of light is dependent on size. Therefore, clear or transparent compositions appear to be single phases without droplets, particles, or domains, when viewed with the naked eye.

Accordingly, the criteria used in this invention for determining optical clarity was whether text could be read with the naked eye through a two centimeter diameter bottle filled with the microemulsion. This is a legitimate criteria as noted in *Microemulsions Theory and Practice*, Leon M. Prince, Academic Press, Inc., Pages 7–10, New York (1977), i.e., "Visual recognition of microemulsions should not be taken lightly. In fact, the microemulsion chemist should train himself carefully in this art. Use of sunlight rather than an artificial source of light is recommended. The eye is better than a microscope because the limit of resolution of a light microscope in blue light is only about 0.1 μm so that droplets smaller than 0.14 μm cannot be seen".

Ternary compositions containing water, a volatile cyclic or linear alkyl siloxane, and a short-chain or low molecular weight silicone polyether can be combined to form clear compositions without the addition of other materials. Thus, the compositions can be free of such non-essential ingredients as salts; co-surfactants; monohydroxy alcohols; and diols and triols such as ethylene glycol and glycerol. The elimination of such non-essential ingredients is especially beneficial and advantageous, as it obviates the need for refractive index matching, often resorted to in the past to achieve clear or transparent products. However, it should be understood that such non-essential ingredients may be included, if desired, without departing from the spirit of the present invention.

The oil, water, and surfactant can be combined in any given order of addition. While heat enhances solubility, lowers surface tension, and reduces viscosity, its application is not required. Room temperature (20–25° C./68–77° F.) is sufficient in most cases.

The oil component of the ternary composition is a cyclic alkyl siloxane of the formula $(R_2SiO)_p$ or linear alkyl siloxane of the formula $R_3SiO(R_2SiO)_qSiR_3$ in which R is an alkyl group containing 1–6 carbon atoms, p is 3–6 and q is 0–5. Most preferred, however, are volatile cyclic methyl siloxanes of the formula $\{(CH_3)_2SiO\}_p$ and volatile linear methyl siloxanes of the formula $(CH_3)_3SiO\{(CH_3)_2SiO\}_qSi(CH_3)_3$ and in which p is 3–6 and q is 0–5, respectively. Preferably, the volatile methyl siloxane has a boiling point less than 250° C. and a viscosity of 0.65–5.0 centistoke (mm²/s).

Some representative linear volatile methyl siloxanes are hexamethyldisiloxane with a boiling point of 100° C., viscosity of 0.65 mm²/s, and formula $Me_3SiOSiMe_3$; octamethyltrisiloxane with a boiling point of 152° C., viscosity of 1.04 mm²/s, and formula $Me_3SiOMe_2SiOSiMe_3$; decamethyltetrasiloxane with a boiling point of 194° C., viscosity of 1.53 mm²/s, and formula $Me_3SiO(Me_2SiO)_2SiMe_3$; dodecamethylpentasiloxane with a boiling point of 229° C., viscosity of 2.06 mm²/s, and formula $Me_3SiO(Me_2SiO)_3SiMe_3$; tetradecamethylhexasiloxane with a boiling point of 245° C., viscosity of 2.63 mm²/s, and formula $Me_3SiO(Me_2SiO)_4SiMe_3$; and hexadecamethylheptasiloxane with a boiling point of 270° C., viscosity of 3.24 mm²/s, and formula $Me_3SiO(Me_2SiO)_5SiMe_3$. Me in these and the following formulas represents the methyl group $CH_3$.

Some representative cyclic volatile methyl siloxanes are hexamethylcyclotrisiloxane, a solid at room temperature, with a boiling point of 134° C. and formula $(Me_2SiO)_3$; octamethylcyclotetrasiloxane with a boiling point of 176° C., viscosity of 2.3 mm²/s, and formula $(Me_2SiO)_4$; decamethylcyclopentasiloxane with a boiling point of 210° C., viscosity of 3.87 mm²/s, and formula $(Me_2SiO)_5$; and dodecamethylcyclohexasiloxane with a boiling point of 245° C., viscosity of 6.62 mm²/s, and formula $(Me_2SiO)_6$.

The third component of the ternary system is a short-chain or low molecular weight silicone polyether. Representative silicone polyethers have average structures represented by:

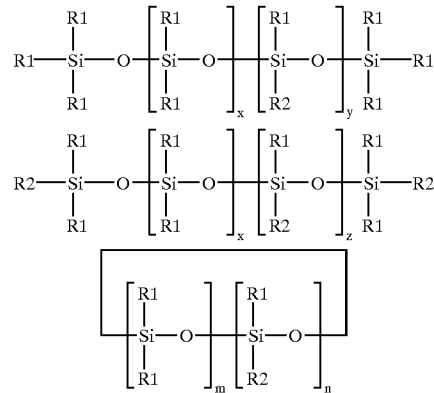

where R1 is an alkyl group containing 1–6 carbon atoms; R2 represents the radical $—(CH_2(_aO(C_2H_4O)_b(C_3H6_{O)_c}R_3$; x has a value of 0–3; y has a value of 1–3; z has a value of 0–2; m has a value of 3–5; n is one; a has a value of 0–6; b has a value of 2–6; c has a value of 0–3; and R3 is hydrogen, a methyl radical, or an acyl radical.

It should be understood that commercial silicone polyethers, by their very nature, contain a distribution of different molecular structures and chain lengths, i.e., as represented by a–c, m, n, and x–y, in the above formulas. Accordingly, silicone polyethers according to the present invention should be interpreted to include not only such natural distributions, but artificially blended silicone polyethers in which the average values of a–c, m, n, and x–z, are as defined above.

Compositions according to the invention contain (i) 0.1 to 9 percent by weight of water; (ii) greater than 80 percent by weight of the alkyl siloxane, preferably 81 to 96.9 percent by weight, most preferably greater than 85 percent by weight; and (iii) 3 to 10 percent by weight of silicone polyether.

EXAMPLES

The following examples are set forth in order to illustrate this invention in more detail. In particular, these examples show the preparation of several water-in-silicone oil microemulsions. Optically clear microemulsions were formed spontaneously at room temperature by merely adding to a vial, de-ionized water, decamethylcyclopentasiloxane, and silicone polyether. Essentially no mixing, stirring, shearing, or input of mechanical energy for agitating the ingredients was required, other than gentle hand shaking. The polyether used in these examples had an average structure represented by:

$$R_1-\underset{\underset{R_1}{|}}{\overset{\overset{R_1}{|}}{Si}}-O-\left[\underset{\underset{R_1}{|}}{\overset{\overset{R_1}{|}}{Si}}-O\right]_x\left[\underset{\underset{R_2}{|}}{\overset{\overset{R_1}{|}}{Si}}-O\right]_y\underset{\underset{R_1}{|}}{\overset{\overset{R_1}{|}}{Si}}-R_1$$

where R1 was methyl, x was zero, y was one, and R2 was —$(CH_2)_3(OC_2H_4)_4OH$. Clarity was established by determining that text could be read through a two centimeter diameter bottle filled with the microemulsion, and it was concluded that the microemulsion therefore contained water domains having an average diameter of less than 100 nanometer (0.1 micron).

Example 1

Using an analytical balance, Model No. AG-204 manufactured by Mettler-Toledo Inc., Worthington, Ohio, there was weighed into a vial, 0.3140 g of silicone polyether, 2.7197 g of decamethylcyclopentasiloxane, and 0.1552 g of water. Using only gentle hand shaking of the vial, a single phase clear microemulsion was formed. This microemulsion contained about 85.3 percent by weight of decamethylcyclopentasiloxane.

Example 2

Using the Mettler-Toledo analytical balance, there was weighed into a vial, 0.9023 g of silicone polyether, 9.015 g of decamethylcyclopentasiloxane, and 0.1245 g of water. Using only gentle hand shaking of the vial, a single phase clear microemulsion was formed. This microemulsion contained about 89.8 percent by weight of decamethylcyclopentasiloxane.

Example 3

Using the Mettler-Toledo analytical balance, there was weighed into a vial, 0.8008 g of silicone polyether, 9.1132 g of decamethylcyclopentasiloxane, and 0.1034 g of water. Using only gentle hand shaking of the vial, a single phase clear microemulsion was formed. This microemulsion contained about 91 percent by weight of decamethylcyclopentasiloxane.

Example 4

Using the Mettler-Toledo analytical balance, there was weighed into a vial, 0.9037 g of silicone polyether, 8.6031 g of decamethylcyclopentasiloxane, and 0.5125 g of water. Using only gentle hand shaking of the vial, a single phase clear microemulsion was formed. This microemulsion contained about 85.9 percent by weight of decamethylcyclopentasiloxane.

Example 5

Using the Mettler-Toledo analytical balance, there was weighed into a vial, 0.703 g of silicone polyether, 8.8367 g of decamethylcyclopentasiloxane, and 0.5161 g of water. Using only gentle hand shaking of the vial, a cloudy solution was formed. However, by heating the cloudy solution to 32° C., a single phase clear microemulsion was formed. This microemulsion contained about 87.9 percent by weight of decamethylcyclopentasiloxane.

The following additional examples illustrate the invention in which clear microemulsions were prepared even though a non-essential component such as salt was included.

Example 6

Using the Mettler-Toledo analytical balance, there was weighed into a vial, 0.9018 g of silicone polyether, 8.6137 g of decamethylcyclopentasiloxane, and 0.5151 g of a solution containing five percent by weight of sodium chloride. Using only gentle hand shaking of the vial, a single phase clear microemulsion was formed. This microemulsion contained about 85.9 percent by weight of decamethylcyclopentasiloxane.

Example 7

Using the Mettler-Toledo analytical balance, there was weighed into a vial, 0.8028 g of silicone polyether, 8.7017 g of decamethylcyclopentasiloxane, and 0.5049 g of a solution containing five percent by weight of sodium chloride. Using only gentle hand shaking of the vial, a single phase clear microemulsion was formed. This microemulsion contained about 86.9 percent by weight of decamethylcyclopentasiloxane.

Example 8

Using the Mettler-Toledo analytical balance, there was weighed into a vial, 0.7023 g of silicone polyether, 8.8045 g of decamethylcyclopentasiloxane, and 0.511 g of a solution containing five percent by weight of sodium chloride. Using only gentle hand shaking of the vial, a single phase clear microemulsion was formed. This microemulsion contained about 87.9 percent by weight of decamethylcyclopentasiloxane.

Example 9

Using the Mettler-Toledo analytical balance, there was weighed into a vial, 0.6116 g of silicone polyether, 8.9076 g of decamethylcyclopentasiloxane, and 0.5095 g of a solution containing five percent by weight of sodium chloride. Using only gentle hand shaking of the vial, a single phase clear microemulsion was formed. This microemulsion contained about 88.8 percent by weight of decamethylcyclopentasiloxane.

The above examples show that microemulsions can be formed spontaneously and are generally stable indefinitely. The order of addition of the components does not influence their formation, and simple hand shaking at room temperature is generally sufficient to cause the microemulsions to form.

This is significant because it is now possible to make clear products without involving the use of high shear previously required to obtain the small size necessary to achieve clarity. These clear microemulsions form spontaneously in the sense that they do not require energy input by means of mixing and shear devices. Thus, turbines, impellers, colloid mills, homogenizers, or sonolators, are not required to form these systems. It is only necessary that the appropriate amounts of the three components be added to a suitable container, and the container hand shaken. Of course, the components can be mixed or sheared with more energy input, and the microemulsions will still be obtained, but no advantage results from such additional energy usage.

The spontaneously formed clear microemulsion is useful in personal care. Thus, it is useful in preparing antiperspirants and deodorants. It can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats. In cosmetics, it can be added to make-ups, color cosmetics, foundations, blushes, lipsticks, eyeliners, mascaras, oil removers, color cosmetic removers, and powders. It can include oil soluble as well as water soluble substances such as vitamins.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A water-in-oil microemulsion comprising (i) 0.1 to 9 percent by weight of water; (ii) greater than 80 percent by weight of a cyclic alkyl siloxane oil having the formula $(R_2SiO)_p$ or a linear alkyl siloxane oil having the formula $R_3SiO(R_2SiO)_qSiR_3$ in which R is an alkyl group containing 1–6 carbon atoms, p is 3–6, and q is 0–5; and (iii) 3 to 10 percent by weight of a silicone polyether having a formula selected from the group consisting of

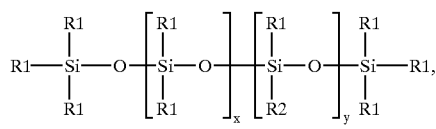

-continued

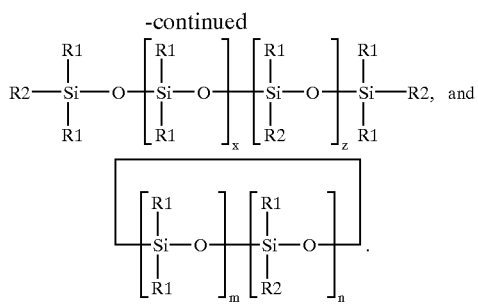

where R1 represents an alkyl group containing 1–6 carbon atoms; R2 represents the radical —$(CH_2(_aO(C_2H_4O)_b(C_3H_6O)_cR_3$; x has a value of 0–3; y has a value of 1–3; z has a value of 0–2; m has a value of 3–5; n is one; a has a value of 0–6; b has a value of 2–6; c has a value of 0–3; and R3 is hydrogen, a methyl radical, or an acyl radical; the water-in-oil microemulsion containing domains of oil or water having an average diameter of less than 100 nanometer (0.1 micron/1,000 angstrom Å).

2. A microemulsion according to claim 1 in which the alkyl siloxane is present in the amount of 81 to 96.9 percent by weight.

3. A microemulsion according to claim 1 in which the alkyl siloxane is present in an amount greater than 85 percent by weight.

4. A microemulsion according to claim 1 in which the alkyl siloxane is octamethylcyclotetrasiloxane, decamethylcyclopentasiloxane, or a mixture of octamethylcyclotetrasiloxane and decamethylcyclopentasiloxane.

5. A personal care product containing the microemulsion of claim 1.

6. A method of treating hair or skin comprising applying to the hair or skin the microemulsion or a composition containing the microemulsion of claim 1.

* * * * *